United States Patent [19]

Warden et al.

[11] Patent Number: 5,261,910
[45] Date of Patent: Nov. 16, 1993

[54] APPARATUS FOR MAINTAINING SPINAL ELEMENTS IN A DESIRED SPATIAL RELATIONSHIP

[75] Inventors: Karen E. Warden, Cleveland, Ohio; William L. Carson, Columbia, Mo.; Terrence M. Stahurski, Rocky River, Ohio

[73] Assignee: AcroMed Corporation, Cleveland, Ohio

[21] Appl. No.: 838,566

[22] Filed: Feb. 19, 1992

[51] Int. Cl.$^5$ ............................................. A61F 5/04
[52] U.S. Cl. ............................................. 606/61
[58] Field of Search ................. 606/61, 69, 72, 73, 606/60

[56] References Cited

U.S. PATENT DOCUMENTS

| | | | |
|---|---|---|---|
| 4,696,290 | 9/1987 | Steffee | 606/69 |
| 4,822,366 | 4/1989 | Bolesky | 623/20 |
| 5,084,048 | 1/1992 | Jacob et al. | 606/61 |
| 5,085,660 | 2/1992 | Lin | 606/61 |
| 5,092,893 | 3/1992 | Smith | 606/61 |
| 5,151,103 | 9/1992 | Tepic et al. | 606/69 |

OTHER PUBLICATIONS

Advertisement for Amset ALPS Anterior Locking Plate System (2 pp.).

Primary Examiner—David Isabella
Attorney, Agent, or Firm—Tarolli, Sundheim & Covell

[57] ABSTRACT

An improved apparatus for maintaining spinal elements in a desired spatial relationship includes a plate and a fastener having a first threaded end portion for engaging a spinal element, a second threaded end portion and a seat portion. The seat portion of the fastener is received in a recess of a plate. The plate has an elongated slot for receiving the fastener that extends along one side of the longitudinal axis of the plate. A circular opening for receiving another fastener is located on the other side of the longitudinal axis and adjacent the slot. The slot extends through the plate in a first direction and the circular opening extends through the plate in a second direction at an angle to the first direction. The slot is defined by opposed slot surfaces extending longitudinally of the plate and arcuate recesses in the opposed slot surfaces and spaced therealong. The recesses in the opposed slot surfaces define a plurality of locations for receiving the fastener. The plurality of locations have centers that are offset from the center of the circular opening. A nut threadably engages the first fastener and engages the arcuate recesses in the opposed slot surfaces to clamp the plate between the seat portion of the fastener and the nut.

10 Claims, 3 Drawing Sheets

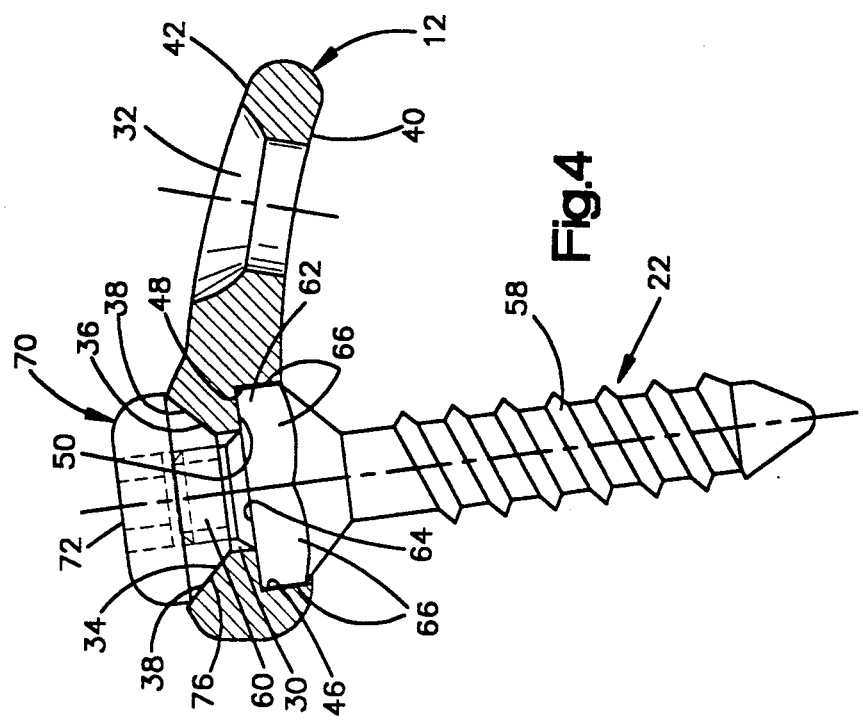
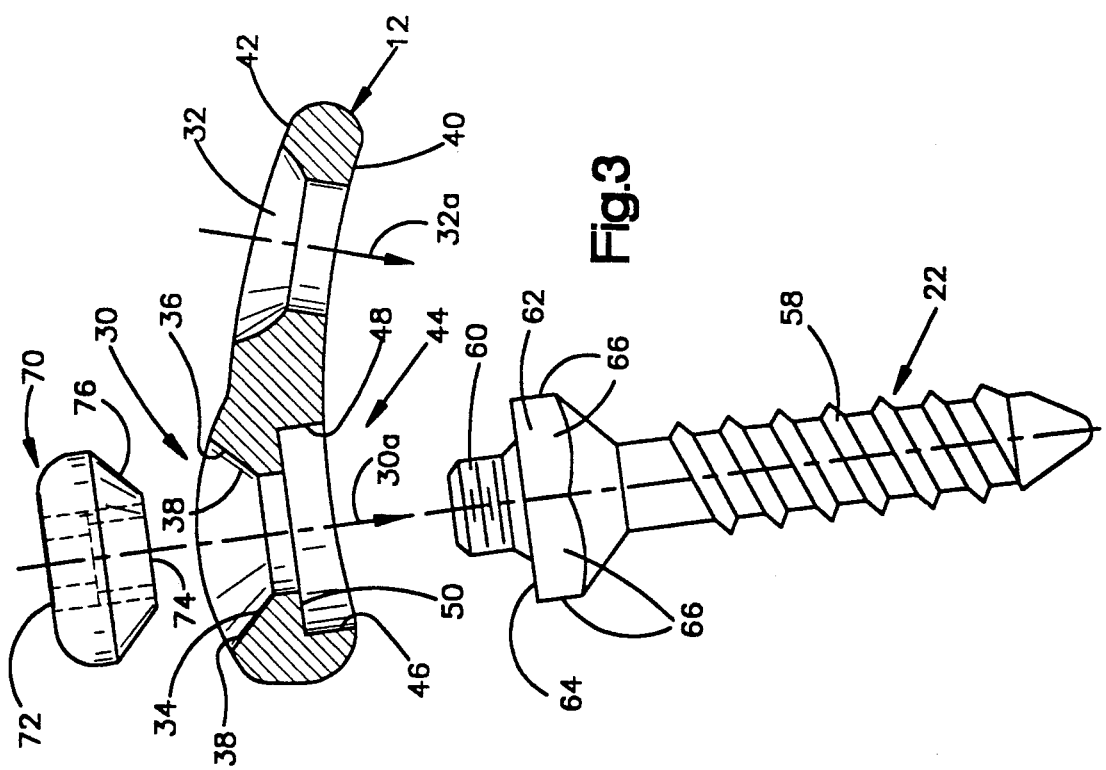

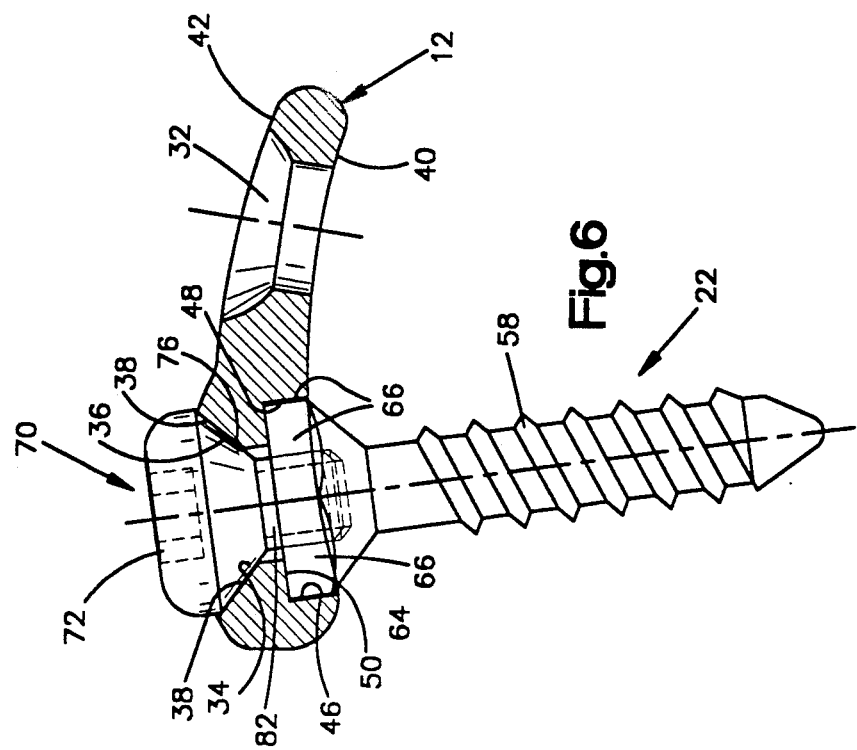
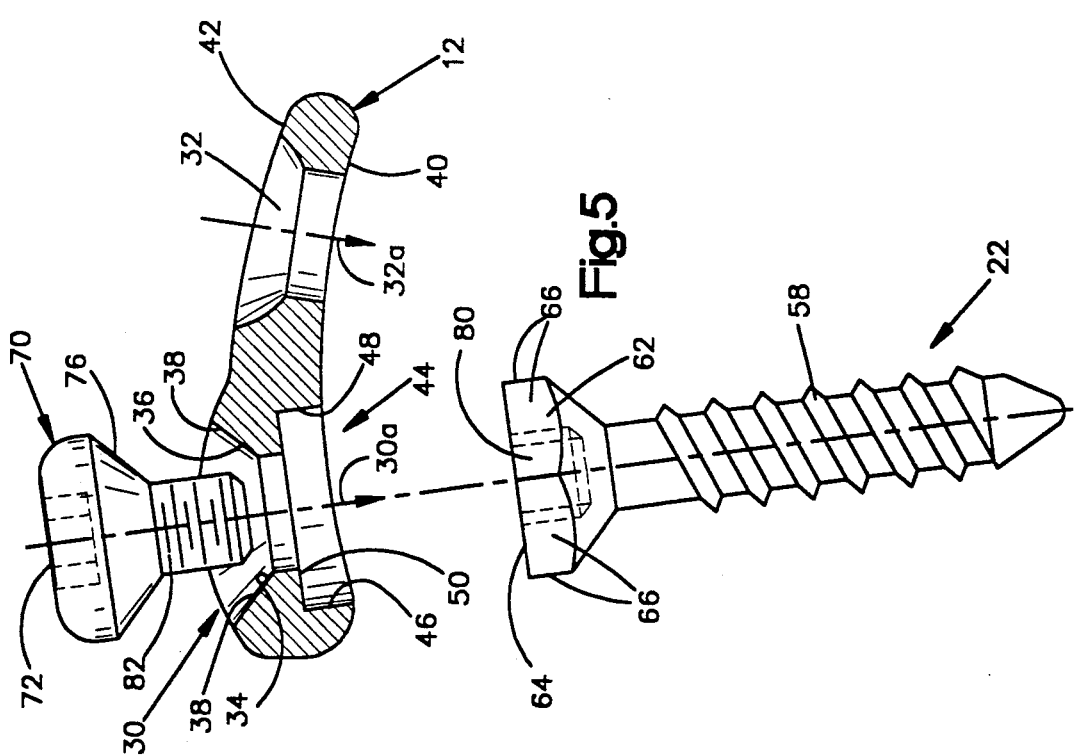

APPARATUS FOR MAINTAINING SPINAL ELEMENTS IN A DESIRED SPATIAL RELATIONSHIP

BACKGROUND OF THE INVENTION

The present invention relates to a new and improved apparatus for maintaining spinal elements in a desired spatial relationship. More specifically, the present invention relates to an apparatus for maintaining cervical vertebrae of a spinal column in a desired spatial relationship.

A known apparatus for maintaining spinal elements in a desired spatial relationship includes a plate having a longitudinally extending slot extending along one side of the longitudinal axis of the plate. A circular opening for receiving a fastener, such as a screw, is located adjacent the slot on the other side of the longitudinal axis. The slot defines a plurality of locations for receiving another screw. The plate is bent about its longitudinal axis so that the slot and the circular opening extend through the plate at an angle to each other.

The center of one of the plurality of locations is aligned with the center of the circular opening, i.e., the centers lie in a plane extending perpendicular to the longitudinal axis of the plate. Thus, the screw extending through the circular opening and the screw extending through the slot may strike each other in the spinal element when the plate is attached to the spinal element.

To attach the plate to the spinal column, a first screw is placed through the slot in the plate and threaded into a spinal element a small amount. The plate is then moved so that the circular opening is in a desired position. A second screw is placed through the circular opening and threaded into the spinal element to fixedly attach the plate to the spinal element. The first screw extending through the slot is then fully driven into the spinal element to further fix the plate to the spinal element. While the second screw is being threaded into the spinal element the plate can rotate relative to the first screw and move out of the desired position.

SUMMARY OF THE INVENTION

The present invention provides a new and improved apparatus for maintaining spinal elements in a desired spatial relationship. The present invention is specifically designed for placement on the anterior cervical portion of the spinal column. Although, it is contemplated that the present invention could be used at any location along the spinal column.

The apparatus includes a plate and fasteners. One fastener has a first threaded end portion for engaging a vertebra, a second threaded end portion and a seat portion. The plate has at least one slot extending along one side of the longitudinal axis of the plate for receiving the one fastener. At least one circular opening for receiving another fastener such as a screw is located on the other side of the longitudinal axis. The slot extends through the plate in a first direction and the circular opening extends through the plate in a second direction at an angle to the first direction to minimize the possibility of the fasteners coming loose from the vertebra.

The slot is defined by opposed slot surfaces extending longitudinally of the plate and arcuate recesses in the opposed slot surfaces and spaced therealong. The recesses in the opposed slot surfaces define a plurality of locations for receiving the one fastener. The plurality of locations have centers that are offset along the longitudinal axis of the plate from the centers of the circular openings. This enables the fasteners to be spaced from each other in the vertebra when the plate is connected to the vertebrae.

The slot is further defined by a longitudinal recess in a side surface of the plate that faces the vertebrae. The recess has a width measured in a direction perpendicular to the longitudinal axis of the recess that is equal to the distance between two parallel side surfaces of the seat portion of the fastener. The recess receives the seat portion of the one fastener. The side surfaces of the seat portion of the one fastener and surfaces defining the recess engage to prevent the plate from rotating relative to the one fastener when the plate is being positioned relative to the vertebrae.

A nut threadably engages the second threaded end portion of the one fastener to clamp the plate to the fastener and the vertebrae and prevent relative movement between the plate and the fastener. The plate is clamped between the nut and the seat portion of the one fastener. The nut has a frustoconical portion that engages the arcuate recess in the slot to block sliding movement of the plate relative to the fastener.

In one embodiment of the present invention, the second threaded end portion of the one fastener extends through the slot in the plate. The second threaded end portion is externally threaded and engages an internally threaded opening in the nut.

In another embodiment of the present invention, the second threaded end portion of the one fastener includes an internally threaded opening. The nut includes an externally threaded portion for engaging the internally threaded opening in the fastener.

When the apparatus is to be connected with the spinal column, the fastener or fasteners that extend into the slot or slots in the plate are threaded into the vertebrae at desired locations. The plate is then placed over the fasteners with the longitudinal recesses in the plate receiving the seat portions of the fasteners. The nuts are then loosely threaded onto the fasteners to connect the plate with the fasteners. The plate can be moved longitudinally relative to the fasteners for positioning the circular openings in desired positions. The nuts are then threaded tightly onto the fasteners to clamp the plate between the seat portions of the fasteners and the nuts. One or a plurality of other fasteners, such as screws, are then screwed into the vertebrae through the circular openings.

BRIEF DESCRIPTION OF THE DRAWINGS

The foregoing and other objects and features of the present invention will become more apparent upon consideration of the following description taken in connection with the accompanying drawings, wherein:

FIG. 3 is an exploded view, partly in section, showing how a fastener, a nut and the plate of the apparatus of FIG. 1 are connected together;

FIG. 4 is a view, partly in section, showing the fastener, the nut and the plate of FIG. 3 connected together;

FIG. 5 is a view, generally similar to FIG. 3, showing a second embodiment of a fastener and a nut connected to the plate; and FIG. 6 is a view, partly in section, showing the fastener, the nut and the plate of FIG. 5 connected together.

DESCRIPTION OF THE PREFERRED EMBODIMENTS

Figures 1, 2:
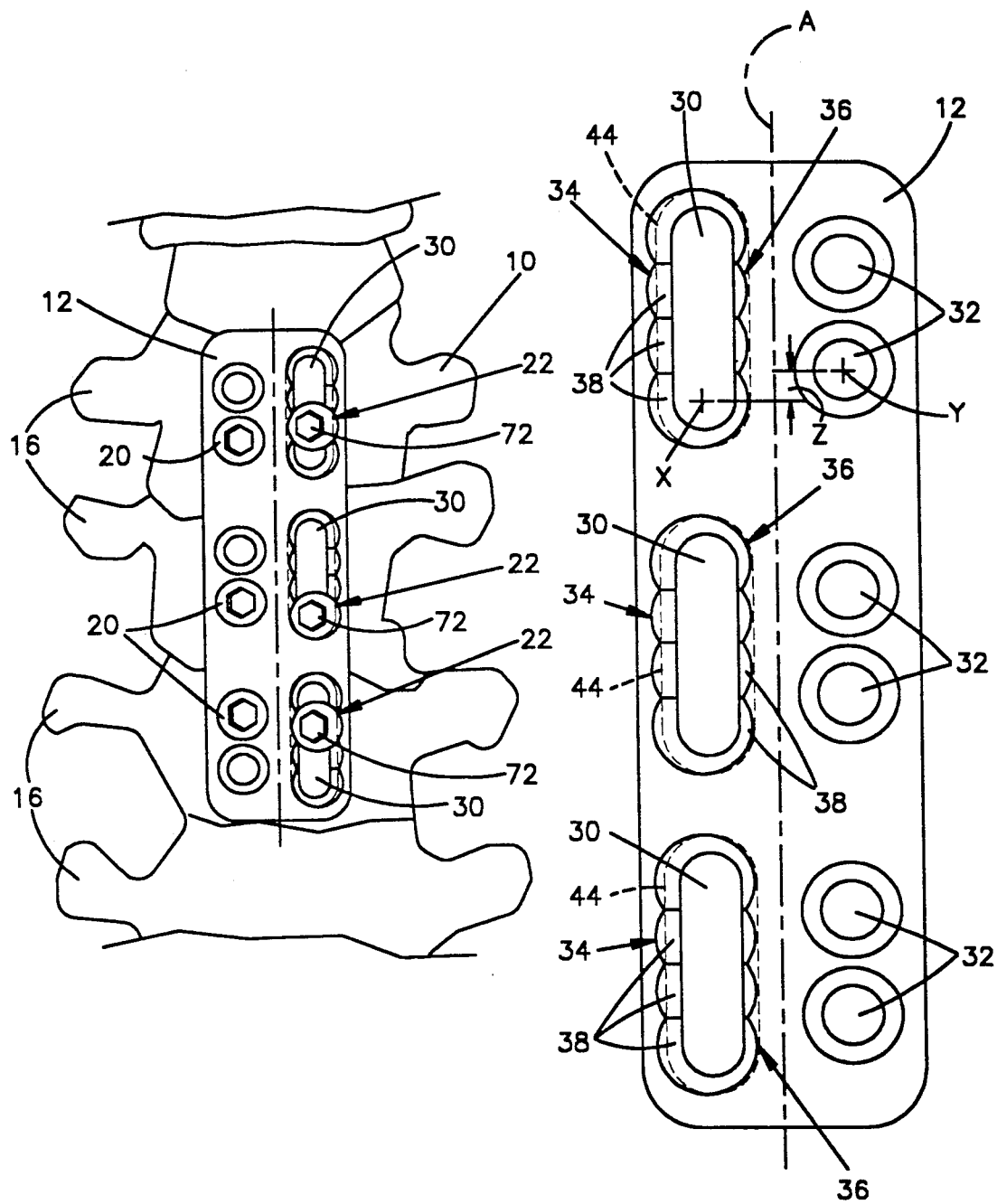
FIG. 1 is a fragmentary view of a portion of a spinal column on which an apparatus constructed in accordance with the present invention has been installed to maintain spinal elements in a desired spatial relationship.
FIG. 2 is a plan view of a plate used in the apparatus of FIG. 1.

The cervical portion of a human spinal column 10 to which a plate 12 is connected is illustrated in FIG. 1. The plate 12 retains portions of the spinal column, that is vertebrae 16, in a desired spatial relationship relative to each other. The plate 12 is made of a bio-compatible material, such as stainless steel, titanium, or a composite. Fasteners 20 and 22 connect the plate 12 to the vertebrae 16. The fasteners 20 are screws with hexagon shaped recesses in the heads of the screws for receiving an Allen wrench to drive the screws into the vertebrae.

The fasteners 20 and 22 are shown as extending in a horizontal plane perpendicular to the axis A of the plate. The plate could be bent or angled washers could be used if it was desired to have the fasteners extend upwardly or downwardly relative to a horizontal plane.

The plate 12 has a length which is at least sufficient to enable the plate to span at least two of the vertebrae 16. In the embodiment of the invention illustrated in FIG. 1, the plate 12 spans three vertebrae 16. Of course, the length of the plate in any particular installation will depend upon the condition to be corrected and the number of vertebrae 16 to be held in a desired spatial relationship relative to each other by the plate 12.

The plate 12 (FIGS. 1-2) includes a plurality of slots 30 into which the fasteners 22 extend. The slots 30 extend along one side of the longitudinal axis A of the plate 12. A plurality of circular openings 32 for receiving the plurality of fasteners 20 extend along the other side of the longitudinal axis A and adjacent to the slots 30. Two circular openings 32 are adjacent each slot 30. There are no slots on the side of the plate having the circular openings 32 and there are no circular openings on the side of the plate having the slots 30.

The slots 30 (FIG. 2) are defined by opposed slot surfaces 34 and 36 extending longitudinally of the plate. The slots 30 are also defined by arcuate recesses 38 (FIGS. 3 and 4) spaced along the opposed slot surfaces 34 and 36. The arcuate recesses 38 in the slot surface 34 are aligned with the recesses 38 in the slot surface 36 to define a plurality of locations for receiving the fastener 20 (FIG. 2). The plurality of locations have centers X (only one is designated in FIG. 2) that are offset along the longitudinal axis A of the plate from the centers Y (only one is designated in FIG. 2) of the circular openings 32. The offset for one opening 32 and one slot location is designated Z in FIG. 2.

The plate 12 is curved about its longitudinal central axis (FIGS. 3 and 4). The slots 30 extend through the plate 12 in a first direction shown by arrow 30a in FIG. 3. The circular openings 32 extend through the plate 12 in a second direction shown by arrow 32a in FIG. 3 at an angle to the first direction. The fasteners 20 and 22 therefore extend through the plate and into the vertebrae 16 at an angle relative to each other. This minimizes the possibility of the fasteners from coming loose.

If the centers X of the plurality of locations were not offset from the centers Y of the circular openings 32 the fasteners 20 and 22 could strike each other in the vertebrae 16 due to the angle between the directions 30a and 32a. The diameters of the fasteners 20 and 22 and the offset between the centers X and Y cooperate to prevent the fasteners from striking each other when the plate 12 is attached to the vertebrae. Thus, the plate 12 is securely attached to the vertebrae 16 by the fasteners 20 and 22.

The fasteners 20 and 22 are shown as extending in a horizontal plane perpendicular to the axis A of the plate. The plate could be bent or angled washers could be used if it was desired to have the fasteners extend upwardly or downwardly relative to a horizontal plane.

The plate 12 has a first major side surface 40 (FIGS. 3 and 4) for facing the vertebrae 16 and a second opposite major side surface 42. Each of the slots 30 are further defined by a longitudinal recess 44 located in the first major side surface 40. The longitudinal recess 44 is defined by a pair of parallel side surfaces 46 and 48. The recess 44 also includes a substantially flat major side surface 50 which may be termed the bottom of the recess. The function of the recess 44 will be hereinafter described.

Each of the fasteners 22 (FIGS. 3 and 4) is a screw having a first threaded end portion 58 for engaging the vertebrae 16 and a second threaded end portion 60. The fastener 22 also includes a seat portion 62 to be located in the recess 44 of the plate 12. The seat portion 62 includes a flat annular upper surface 64 for engagement with the major side surface 50 of the recess 44 (FIG. 4). The seat portion 62 also includes wrenching flats 66. Two of the wrenching flats 66 extend parallel to each other and engage the side surfaces 46 and 48 of the recess 44. The distance between the parallel wrenching flats 66 is slightly less than the width of the longitudinal recess 44 measured in a direction perpendicular to the longitudinal axis of the recess. The wrenching flats 66 and the recess 44 prevent the plate 12 from rotating relative to the fastener 22 prior to clamping the plate 12 to the fastener 22 with a nut 70. In addition, the recess minimizes the overall height of the assembled plate and fastener.

The nut 70 includes a hexagon shaped recess 72 (FIGS. 1 and 3) for receiving a wrench for threading the nut 70 onto the threaded end portion 60 of the fastener 22. The nut 70 also includes an internally threaded opening 74 (FIGS. 3 and 4) for threaded engagement with the second threaded end portion 60 of the fastener 22. A frustroconical surface 76 of the nut 70 engages an arcuate recess 38 defined in the slot surfaces 34 and 36 to block sliding movement of the plate relative to the fastener 22 when the plate is clamped to the fastener 22. The nut 70 is threaded onto the fastener 22 to clamp the plate between the nut 70 and the seat portion 62 of the fastener.

In the second embodiment of the present invention illustrated in FIGS. 5 and 6, the second threaded end portion 60 of the fastener 22 is replaced with an internally threaded opening 80. The internally threaded opening 74 in the nut 70 is replaced with an externally threaded portion 82. The threaded portion 82 of the nut 70 extends through the slot 30 and threadably engages the opening 80 in the fastener 22 to clamp the plate 12 to the fastener 22.

When the plate 12 is to be connected to the vertebrae 16, the fasteners 22 are driven into the vertebrae at their desired positions. The plate 12 is then positioned with the seat portions 62 of the fasteners 22 extending into the recesses 44 of the plate 12. The nuts 70 are then loosely threaded onto the fasteners 22. The plate 12 can be moved longitudinally to position the circular openings 32 in desired positions.

Once the plate 12 has been positioned relative to the fasteners 22 with the circular openings 32 in their desired positions the nuts 70 are tightened onto the fasteners 22. The nuts 70 clamp the plate 12 between the seat portion 62 of the fasteners 22 and the nut 70. Thus, the plate 12 is prevented from moving relative to the spinal elements and the fasteners 22. The fasteners 20 are then driven into the vertebrae 16 to further fix the plate relative to the vertebrae 16.

From the above description of the invention, those skilled in the art will perceive improvements, changes and modifications. Such improvements, changes and modifications within the skill of the art are intended to be covered by the appended claims.

Having described the invention, the following is claimed:

1. A biocompatible implant apparatus for maintaining spinal elements in a desired spatial relationship, said apparatus comprising:

a fastener having a first threaded end portion for engaging a spinal element, a second threaded end portion and a seat portion;

a plate having a length sufficient to enable the plate to span at least two of the spinal elements a first opening into which said fastener extends; and a nut for threadably engaging said second threaded end portion of said fastener to prevent relative movement between said plate and said fastener, said plate being clamped between said nut and said seat portion;

said plate having surfaces defining a recess in alignment with said first opening for receiving said seat portion of said fastener and said surfaces defining said recess comprising means for preventing relative rotation between said plate and said fastener prior to said plate being clamped between said nut and said seat portion.

2. An apparatus as set forth in claim 1 wherein said recess extends along said plate in a longitudinal direction, said recess having a width measured in a direction perpendicular to the longitudinal direction, said seat portion having flat parallel side surfaces, the distance between said flat parallel side surfaces of said seat portion being substantially equal to the width of said recess.

3. An apparatus as set forth in claim 1 wherein said seat portion of said fastener includes wrenching flats for driving said fastener into the spinal element.

4. An apparatus as set forth in claim 1 wherein said second threaded end portion extends through the first opening in said plate and said nut has an internally threaded opening, the internal threads of said nut threadably engaging said second threaded end portion.

5. An apparatus as set forth in claim 1 wherein said second threaded end portion of said fastener includes an internally threaded opening and said nut includes an externally threaded portion for engaging the internally threaded opening in said fastener.

6. An apparatus as set forth in claim 1 wherein said plate includes a second opening through which a fastener is extendable, the first opening extending through said plate in a first direction and the second opening extending through said plate in a second direction at an angle to the first direction.

7. An apparatus as set forth in claim 6 wherein said plate is curved so that the second direction extends at said angle to the first direction.

8. An apparatus as set forth in claim 6 wherein said plate includes a longitudinally extending slot means, said slot means defining the first opening into which said fastener extends, said slot means being defined by opposed slot surfaces extending longitudinally of said plate and arcuate recesses in said opposed slot surfaces spaced therealong, the recesses in one of said opposed slot surfaces being aligned with the recesses in the other of said slot surfaces to define a plurality of locations for receiving said fastener, each of said plurality of locations having a center that is offset from the center of said second opening.

9. An apparatus as set forth in claim 1 wherein said plate includes a longitudinally extending slot means, said slot means defining the first opening into which said fastener extends, said slot means being defined by a plurality of frustoconical recesses spaced along said slot means to define a plurality of locations for receiving said fastener, the recesses comprising means for blocking sliding movement of said plate relative to said fastener.

10. An apparatus as set forth in claim 9 wherein said nut includes a frustoconical portion that is received in one of said plurality of frustoconical recesses.

* * * * *